United States Patent [19]

Cane

[11] Patent Number: 4,963,903
[45] Date of Patent: Oct. 16, 1990

[54] CAMERA POSITIONING SYSTEM

[76] Inventor: Richard M. Cane, 6142 Miramar Pkwy., Miramar, Fla. 33023

[21] Appl. No.: 426,290

[22] Filed: Oct. 25, 1989

[51] Int. Cl.$^5$ .............................................. G03B 29/00
[52] U.S. Cl. ..................................................... 354/81
[58] Field of Search ........................................... 354/81

[56] References Cited

U.S. PATENT DOCUMENTS 2,464,067  3/1949  Barker ..................................... 354/81
3,891,301  6/1975  Heller ................................. 354/81 X Primary Examiner—Michael L. Gellner
Attorney, Agent, or Firm—Melvin K. Silverman

[57] ABSTRACT

A system for positioning a camera relative to a work area including a clamp means situated outside of the work area, and extension and support element which operates to maintain a given position thereof. The system further includes camera mechanically held within a socket at an end of said position retention element. A high resolution solid state and miniature video TV camera serves as said camera. The system offers a simple, convenient method of close-up monitoring or video taping in which the video camera can be positioned directly over the area of surgical operation or industrial inspection. The camera can be easily moved and rotated to any position offering extreme macro close-ups, which close-ups can be video taped for later use in educational and quality control processes.

22 Claims, 1 Drawing Sheet

000
CAMERA POSITIONING SYSTEM

BACKGROUND OF THE INVENTION

The present invention relates to a system for the positioning of a camera relative to a work area and, in addition, to a specially adapted flexible mouth which utilizes a miniature video camera to position and focus the camera in crowded and/or difficult to reach areas. Such a video camera may be employed in monitoring and/or video taping in association with close-up surgery and close-range industrial inspections.

The instant invention attempts to improve on prior art methods of monitoring and recording surgical procedures at extremely close ranges. More particularly, in the prior art, a camera is mounted near or behind a surgeon and is therefore difficult to use in that such camera will shoot at it at an angle and, therefore, it is field of the view will be blocked by the surgical team. In general, to avoid this problem, it is necessary for the camera operator to adjust camera position, focus, and zoom. To achieve this, the field of view is not directly over the body cavity and, accordingly, close-ups of the surgical procedure cannot be effected.

With further respect to the prior art, an overhead mounted camera presents difficulties in that high wattage surgical lights must be positioned over the body cavity thereby blocking a view of the cavity. These, in addition to the problems of power consumption, will obstruct the view of the camera. Further, it is impractical to mount a camera under the surgical lights in that the result will be that of positioning the camera close to the body cavity thus rendering still camera conditions difficult to maintain. As well, focusing at such close distance is not feasible with most lenses.

With further regard to the prior art, and as such is exemplified in U.S. Pat. No. 3,919,475 (1975) to Dukich entitled Head Attached Television, and in U.S. Pat. No. 4,616,257 (1986) to Kloots, entitled Headlight, a surgeon head mounted camera is not able to utilize a large enough lens for the intended purpose, thereby restricting such system to the use of a small lens capable of producing a wide angle view but not, however, capable of producing an extreme macro view deep within the body cavity, which is desired by most surgeons. Further, the prior art as reflected in Dukich and Kloots above requires that the surgeon keep his head perfectly still to produce a viewable picture. This is, of course, not realistic in that a surgeon must be free to move his head whenever and however he wishes during a surgical procedure.

The present invention is accordingly intended to provide an easy, convenient method of mounting a miniature solid state, high resolution color video camera within the context of a simple flexible mounting having a precision clamp that can be easily attached directly to overhead surgical lights, surgical columns, or the operating table itself. The instant invention also envisions a flange mount which can be utilized instead of a clamp for fixing the mounting to a wall or ceiling where a more permanent installation is required.

The present invention makes use of a flexible extension element which enables the video camera to reach that area necessary to provide enlarged pictures of areas deep within the body cavity without interfering with the work of the surgical team. The result is that extreme macro close-ups, that are ideal for student teaching and maintenance of surgical records on video tapes.

Other prior art known to the inventor which relates to the instant invention includes U.S. Pat. No. 2,111,368 (1938) to Kron, entitled Tilting Camera Support; U.S. Pat. No. 2,510,198 (1950) to Tesner, entitled Flexible Positioner; and U.S. Pat. No. 3,739,095 (1973) to Alden, entitled Scanning Apparatus. While this prior art discloses that the use of a gooseneck-like support structure in connection with a camera has appeared in the art, the instant invention as set forth herein is not shown or suggested in any art known to the inventor.

SUMMARY OF THE INVENTION

The present invention defines a system for the positioning of a camera relative to a work area. The system includes clamp means situated outside of the work area. Depending from said clamp means, a flexible extension and support element comprising a multiplicity of co-active mated segments, said segments, in combination, defining at any segment interface thereof, a potential radius of at least X centimeters, said extension and support element having a length sufficient to reach said work area from said clamp means.

The system further includes electrically means disposed axially within said extension and support element. Socket means integrally depend from said extension support element at that end of said support element opposite said clamp means. The system yet further includes a camera mechanically held within said socket means and in electrical communication with said electrical means. The camera is controlled through the use of remote control means which are in electrical communication with said electrical means within said support element.

It is accordingly an object of the instant invention to provide a system particularly adapted for close range video taping and monitoring of surgical procedures in a crowded surgical environment.

It is another object of the present invention to provide a system for close-range video taping and monitoring in an industrial environment.

It is a further object of the present invention to eliminate the need for the use of a tripod and large dimension camera near a surgical operating table or expensive custom mounted overhead camera systems.

It a yet further object to provide a system including a video tape camera in which the camera can conveniently be brought close to the surgical field and in which a small area deep within the body cavity can be enlarged to obtain extreme macro close-up views suitable for later use in student teaching and in surgical record keeping, by employing the video tapes resultant from the use of the present system.

The above and yet other objects and advantages of the present invention will become apparent in the hereinafter set forth Detailed Description of the Invention, the Drawings, and claims appended herewith.

DETAILED DESCRIPTION OF THE INVENTION

Figure 1:
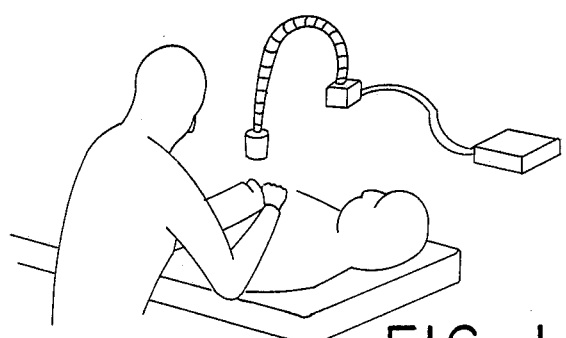
FIG. 1 is an environmental view showing the inventive camera system in operation during a surgical procedure.

With reference to the environmental view of FIG. 1, the inventive system is seen to include clamp means 10 which are secured to a surgical column 12. It is to be noted that said clamp means is situated outside of the work area and, in photographic terms, outside of a field of view of the camera. In actuality, camera 14 will, in most applications, be directed away from the area in which clamp means 12 is secured to a suitable support such as surgical column 12.

With further respect to FIG. 1, there is shown a flexible extension and support element 16 which is formed of a multiplicity of co-active mated segments which, in combination, define at any interface thereof, having a potential radius of at least 15 centimeters. The support element 16 will, therefore, be in the nature of a gooseneck member having, in most applications a length of about 90 centimeters and a weight of about 4 kilograms. The extension support element 16 may be coated with a polyvinyl chloride jacket or silicone rubber heat shrink tubing to provide an aesthetic appearance and a surface which can be easily kept clean.

Within support element 16 is an axially disposed cable, such as a camera cable. At the unmounted end of support element 16 is provided a socket means 18 integrally depending from the support element.

A suitable equivalent for support element 16 would include an articulating arm.

The video camera 14 is mechanically held within socket means 18 and is in electrical communication with said camera cable.

Not shown in the view of FIG. 1 is remote servo-control means which are employed to remotely position camera 14 during a surgical procedure. One form of the remote control 20 is shown in the view of FIG. 2.

Figure 3:
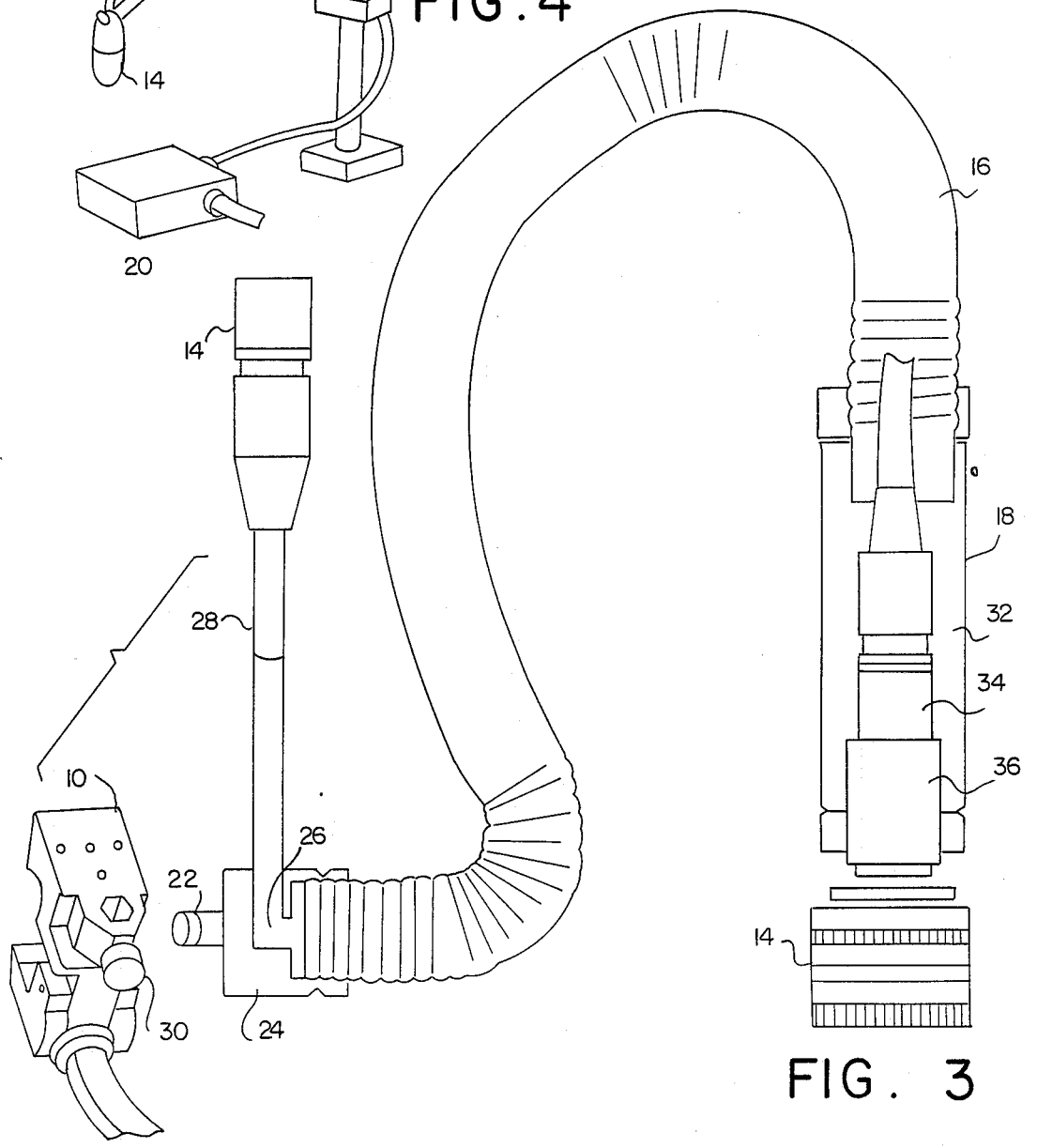
FIG. 3 is a schematic view showing the respective mechanical elements of the camera system.

In the detailed view of FIG. 3, the structure of clamp 10 may be seen as well as the structure of a clamp mounting stud 22 and a delrin mount 24.

Figure 2:
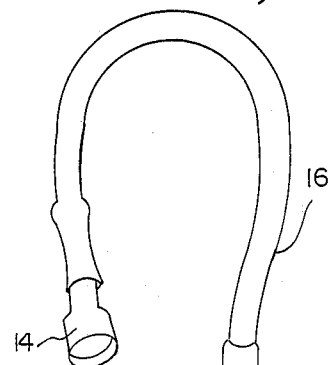
FIG. 2 is a perspective view showing the camera system clamped on a table top, and showing separately the control unit therefor.

In the embodiment of FIG. 3, one may also note that camera cable 26 exits extension and support element 16 near clamp mounting stud 22 and, therefrom, passes into remote control cable 28 which connects to the remote camera control shown in FIG. 2.

With further reference to FIG. 3, it is to be noted that the mouth of clamping means 10 can open to a diameter of about 50 millimeters and can engage surfaces which are flat, square or rounded.

Extension and support element 16 (the gooseneck element) can be swiveled relative to clamp means 10 through the use of thumb screw adjustment means 30.

Video camera 14 comprises a high resolution color CCD solid state miniature TV camera head mounted within said socket means 18 which, in particular, comprises a combination of a delrin grip 32, a connector 34 and a camera head 36.

Where sterilization is necessary, a disposable polyethylene surgical drape may be slipped over the entire unit up to clamp 10, and the system is commercially provided as a completely waterproof, soakable unit which can be disinfected by emerging into solution of cidex dialdehyde.

It is to be appreciated that the use of a gooseneck-like structure having a bend radius of at least 15 centimeters is highly suitable to the present application in that the gooseneck comprises a flexible arm which will retain virtually any position and will enable the camera 14 to be positioned for extreme close-ups without concern of movement of the camera. Camera 18 may also be twisted up to 180 degrees by virtue of the use of said co-active mated segments of element 16 to assist in precision positioning.

The combined weight of extension and support means 16 and video camera 14 with its related apparatus is approximately 7 kilograms.

The camera itself is equipped with a CCD sensor having 300,000 pixels which yield more than 360 lines of resolution. The electronics of the video system provide for a so-called white balance sensor circuit which constantly corrects the white balance level, thereby optimizing color rendition at all times, regardless of varying ambient light conditions. The electronics also provide for a noise reduction circuit in which the signal-to-noise ratio is vastly improved to thusly provide high color quality and signal quality at all light levels. The camera is also provided with a 1/1000 of a second electronic high speed shutter; selective from 1/60 normal to 1/1000 second in which the higher shutter speed will track very rapid medical and industrial operation motions thusly producing clear still frames and slow motion upon VCR playback.

The system also is furnished with the capability of automatic switching of internal/external synchronization, and is genlockable providing for easy adaptation to ready existing systems and/or to provide itself with internal synchronization.

The camera mounting consisting of said elements 32, 34 and 36 may be used with any standard C-mount lens up to 50 millimeters or in series with newer type miniature lenses as employed in special applications where size is a factor, e.g. in close-up dental procedures.

The system may be operated upon any 12 volt DC source or battery and, therefore, is ideal for portable use in various special applications.

In a preferred embodiment, it has been found that it is desirable that the diametric cross-section of camera 14 be no greater than Z times the diametric cross-section of the extension and support element 16. If is further preferred that said video camera 14 have a diametric cross-section in the range of A to B millimeters.

Further, an optimal weight of said support element 16 has been found to be that of about 50 grams per linear centimeter in that excessive weight of support element 16 will de-stabilize the interfaces of said co-active mated segments of said support element 16.

Also, it has been found desirable that the weight of the camera assembly be approximately equal to the overall weight of support element 16, this also being necessary to avoid the de-stabilization of the interfaces of the co-active mated segments of support element 16.

Within a further embodiment the electrical cable 26 may be replaced by photo electrical means such as optical fiber.

Figure 4:
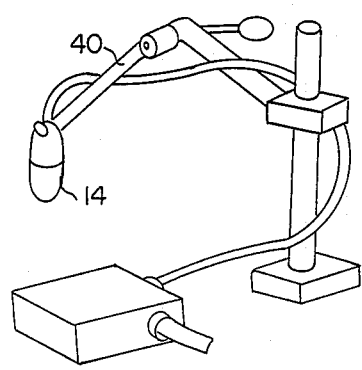
FIG. 4 is a perspective view of a second embodiment of the invention, making use of an articulating arm.

With reference to FIG. 4 there is shown a second embodiment of the invention in which the flexible extension and support element comprises an articulating arm 40.

Accordingly, while there has been shown and described the preferred embodiment of the present invention, it will be understood that the invention may be embodied otherwise than is herein specifically illustrated and described and that, within said embodiment, certain changes may be made in the detail and construction, in the form and arrangement of the parts without departing from the underlying idea or principles of this invention within the scope of the claims appended herewith.

Having thus described my invention, what I claim as new, useful and non-obvious and, accordingly, secure by Letters Patent of the United States is:

1. A system for positioning a camera relative to a work area, the system comprising:
   (a) clamp means situated outside of said work area;
   (b) depending from said clamp means, a flexible extension and support element comprising a multiplicity of co-active mated segments, said segments in combination defining, at any interface thereof a potential radius, said extension and support element having a length sufficient to reach said work area from said clamp means;
   (c) electrical means disposed axially within said extension and support element;
   (d) socket means integrally depending from said support element at that end of said support element opposite said clamp means;
   (e) a camera mechanically held within said socket means and in electrical communication with said electrical means; and
   (f) means for remote control of said camera, said control means in electrical communication means with said electrical means.

2. The system as recited in claim 1, said work area comprising:
   a photographic field of view.

3. The system as recited in claim 1, in which said electrical means comprises:
   a camera cable.

4. The system as recited in claim 3, in which said camera comprises:
   a video camera.

5. The system as recited in claim 3, in which said camera includes a diametric cross-section not greater than three times the diametric cross-section of said extension and support element.

6. The system as recited in claim 3, in which the external housing of said camera comprises a diametric cross-section of about 25 millimeters.

7. The system as recited in claim 6, in which said camera comprises:
   a diametric cross-section not greater that three times the diametric cross-section of said extension and support element.

8. The system as recited in claim 4, in which said clamp means comprises:
   means for mounting an overhead location outside of said work area.

9. The system as recited in claim 4, in which said clamp means comprises:
   means mounted to a desk location outside of said work area.

10. The system as recited in claim 4, in which said camera comprises:
    a weight less that 4 kilograms.

11. The system as recited in claim 4, in which said extension and support element comprises:
    position retention means.

12. The system as recited in claim 11, in which the linear lens of said positioning retention means is at least 90 centimeters.

13. The system as recited in claim 4, in which said position retention means comprises:
    a weight of about 50 grams per linear centimeters thereof.

14. The system as recited in claim 13, in which said camera possesses a weight of less than 4 kilograms.

15. The system as recited in claim 14, in which the weight of said camera to the weight of said position retention means are approximately equal.

16. The system as recited in claim 4, in which said electrical means comprises:
    photo-electrical means.

17. The system as recited in claim 16, in which said photo electrical means comprises:
    optic fibers.

18. A system for positioning a camera relative to a work area, the system comprising:
    (a) clamp means situated outside of said work area;
    (b) depending from said clamp means, a flexible extension and support element comprising an articulating arm, said extension and support element having a length sufficient to reach said work area from said clamp means;
    (c) socket means integrally depending from said support element at that end of said support element opposite said clamp means;
    (d) a camera mechanically held within said socket means;
    (e) means for remote control of said camera;

19. The system as recited in claim 1, said work area comprising:
    a photographic field of view.

20. The system as recited in claim 1, in which said electrical means comprises:
    a camera cable.

21. The system as recited in claim 3, in which said camera comprises:
    a video camera.

22. The system as recited in claim 3, in which said camera includes a diametric cross-section not greater than three times the diametric cross-section of said extension and support element.

* * * * *